(12) United States Patent
Demetrescu et al.

(10) Patent No.: US 10,334,830 B2
(45) Date of Patent: Jul. 2, 2019

(54) ROBOTICS SYSTEM FOR CULTURING AND CONDUCTING EXPERIMENTS ON CAENORHABDITIS ELEGANS

(71) Applicants: Anthony Constantin Demetrescu, Irvine, CA (US); Elijah Jungmin Kim, Laguna Niguel, CA (US); Cedric Jae Tupas Parsons, Mission Viejo, CA (US); Arjun Brannon Ponmalai, Laguna Niguel, CA (US); Ravi Brannon Ponmalai, Laguna Niguel, CA (US)

(72) Inventors: Anthony Constantin Demetrescu, Irvine, CA (US); Elijah Jungmin Kim, Laguna Niguel, CA (US); Cedric Jae Tupas Parsons, Mission Viejo, CA (US); Arjun Brannon Ponmalai, Laguna Niguel, CA (US); Ravi Brannon Ponmalai, Laguna Niguel, CA (US)

( * ) Notice: Subject to any disclaimer, the term of this patent is extended or adjusted under 35 U.S.C. 154(b) by 431 days.

(21) Appl. No.: 15/350,011

(22) Filed: Nov. 12, 2016

(65) Prior Publication Data
US 2017/0142945 A1    May 25, 2017

Related U.S. Application Data

(60) Provisional application No. 62/257,738, filed on Nov. 20, 2015.

(51) Int. Cl.
| | | |
|---|---|---|
| A01K 67/033 | (2006.01) | |
| B25J 9/16 | (2006.01) | |
| G01N 35/10 | (2006.01) | |
| C12M 1/02 | (2006.01) | |
| G01N 35/00 | (2006.01) | |
| B01F 11/00 | (2006.01) | |
| B25J 9/02 | (2006.01) | |

(52) U.S. Cl.
CPC ........ *A01K 67/033* (2013.01); *B01F 11/0005* (2013.01); *B25J 9/023* (2013.01); *B25J 9/1694* (2013.01); *C12M 1/02* (2013.01); *G01N 35/0099* (2013.01); *G01N 35/10* (2013.01)

(58) Field of Classification Search
CPC . B01F 11/00005; B01F 11/0005; C12M 1/02; G01N 35/0099; G01N 35/10; G01N 35/1002; G01N 2035/0422
USPC ....... 422/62–65, 67; 366/110, 111, 209–211, 366/215, 216
See application file for complete search history.

(56) References Cited

U.S. PATENT DOCUMENTS

| | | | | |
|---|---|---|---|---|
| 2,625,906 A | * | 1/1953 | Forney | A01K 41/06 119/325 |
| 5,122,342 A | * | 6/1992 | McCulloch | G01N 35/00732 422/65 |
| 5,206,568 A | * | 4/1993 | Bjornson | G01N 21/253 318/568.1 |

(Continued)

*Primary Examiner* — Michael C McCullough

(57) ABSTRACT

The present invention provides a robotic system for culturing and conducting experiments on *C. elegans* comprising a nutating tower, a well plate positioner, a reagent assembly, a liquid dispensing assembly, a wash and camera assembly, a housing assembly, a tip tray, and a three axes positioner wherein the nutating tower stores and nutates well plates. The present invention further provides a method of using the above-described system to culture *C. elegans*.

20 Claims, 17 Drawing Sheets

(56) References Cited

U.S. PATENT DOCUMENTS

| | | | | |
|---|---|---|---|---|
| 5,409,312 | A * | 4/1995 | Fletcher | B01F 11/0014 366/208 |
| 5,431,201 | A * | 7/1995 | Torchia | A61J 1/20 141/100 |
| 5,511,879 | A * | 4/1996 | Fletcher | B01F 11/0014 366/208 |
| 5,665,309 | A * | 9/1997 | Champseix | G01N 35/04 141/130 |
| 6,991,766 | B2 * | 1/2006 | Roth | B01J 19/0046 211/77 |
| 9,329,194 | B2 * | 5/2016 | Fritchie | B01L 3/5085 |
| 10,184,104 | B2 * | 1/2019 | Lianides | C12M 41/48 |
| 2004/0002163 | A1 * | 1/2004 | Reinhardt | B01L 9/52 422/63 |
| 2004/0170082 | A1 * | 9/2004 | Heeg | C12M 23/48 366/110 |
| 2005/0058574 | A1 * | 3/2005 | Bysouth | G01N 15/0227 422/63 |
| 2007/0116611 | A1 * | 5/2007 | DeMarco | G01N 30/82 422/400 |
| 2008/0180842 | A1 * | 7/2008 | Kaufmann | B01F 11/0008 366/208 |
| 2009/0325274 | A1 * | 12/2009 | Hamada | G01N 35/026 435/286.2 |
| 2011/0085409 | A1 * | 4/2011 | Malin | A61B 10/0096 366/109 |
| 2015/0338428 | A1 * | 11/2015 | Holmes | G01N 35/026 506/2 |
| 2018/0020659 | A1 * | 1/2018 | Camenisch | G01N 35/0099 414/277 |
| 2018/0074082 | A1 * | 3/2018 | Glezer | B01F 11/0014 |
| 2019/0039034 | A1 * | 2/2019 | Siow | B01F 11/0014 |

\* cited by examiner

ROBOTICS SYSTEM FOR CULTURING AND CONDUCTING EXPERIMENTS ON CAENORHABDITIS ELEGANS

CLAIM OF BENEFIT OF FILING DATE

This application claims the benefit of U.S. Provisional Application Ser. No. 62/257,758 titled: "Robotic System for Culturing and Conducting Experiments on *Caenorhabditis Elegans*" filed on Nov. 20, 2015.

FIELD OF INVENTION

The present invention relates to a robotic system for culturing and conducting experiments on the *Caenorhabditis elegans* ("*C. elegans*").

BACKGROUND OF THE INVENTION

*C. elegans* has been widely used in biological research worldwide because it is a simple organism that can be easily transformed with transgenes and the first animal to have its entire genome sequenced having approximately 100 million base pairs of DNA. It is especially useful in genetic modification experiments. The following steps are generally required in order to culture and conduct experiments on the *C. elegans* worms: (i) keep the worms in separate wells of a well plate and in a bacterial suspension which acts as their food (and potential transgene) sources; (ii) agitate the well plates constantly in order to keep the bacteria in suspension; (iii) remove the old bacteria suspension from each well at least once per day; (iv) wash these worms with a buffer solution; (v) take images of the worms within each well in order to collect the experimental data; (vi) replenish the bacterial suspension within each well; and repeat this process for two to three weeks with as much wells as desired for high throughput experiments. Unfortunately, most, if not all, of these steps are currently done manually.

SUMMARY OF INVENTION

The present invention provides a robotic system for culturing and conducting experiments on *C. elegans* that replaces the labor-intensive manual processes described above for *C. elegans*' gene modification experiments and saves countless man-hours and provides significantly higher throughput. The system includes: a nutating tower, a well plate positioner, a reagent assembly, a liquid dispensing assembly, a wash and camera assembly, a housing assembly, a tip tray, and a three axes positioner wherein the nutating tower stores and nutates well plates.

The present invention further provides a method of using the above-described system to culture *C. elegans* comprising of: (i) placing a predetermined number of well plates, having wells containing *C. elegans* bathing in predetermined bacterial solutions, into the nutating tower; (ii) nutating the well plates stored within the nutating tower in order to keep the bacteria in suspension within each well; (iii) stopping the nutating motion of the nutating tower and removing a designated well plate and its lid from the nutating tower using the well plate positioner; (iv) removing the lid from the well plate using the well plate positioner and an electromagnet; (v) removing bacterial solution from a designated well by a vacuum needle of the washing and camera assembly; (vi) washing *C. elegans* in the well by providing fresh buffer solution to the designated well via a buffer needle of the washing and camera assembly and thereafter removing the buffer solution and repeat this step for at least two times; (vii) providing fresh buffer solution to the designated well; (viii) imaging the worms within the designated well with a camera of the washing and camera assembly; (ix) removing the buffer solution from the designated well; (x) repeating step v to step ix for each of the wells of the well plate containing *C. elegans*; (xii) adding predetermined fresh bacterial solutions from the regent assembly to each of the designated wells using the liquid dispensing assembly and the well plate positioner; (xiii) placing the well plate back into the nutating tower; (xiv) nutating the well plates stored within the nutating tower nutating the well plate shelves 64; (xv) repeating step iii to step xiv for all of the designated well plates stored in the nutating tower.

BRIEF DESCRIPTION OF THE DRAWINGS

The features and inventive aspects of the present invention will become more apparent upon reading the following detailed description, claims, and drawings, of which the following is a brief description:

DETAILED DESCRIPTION OF THE INVENTION

Figure 1:
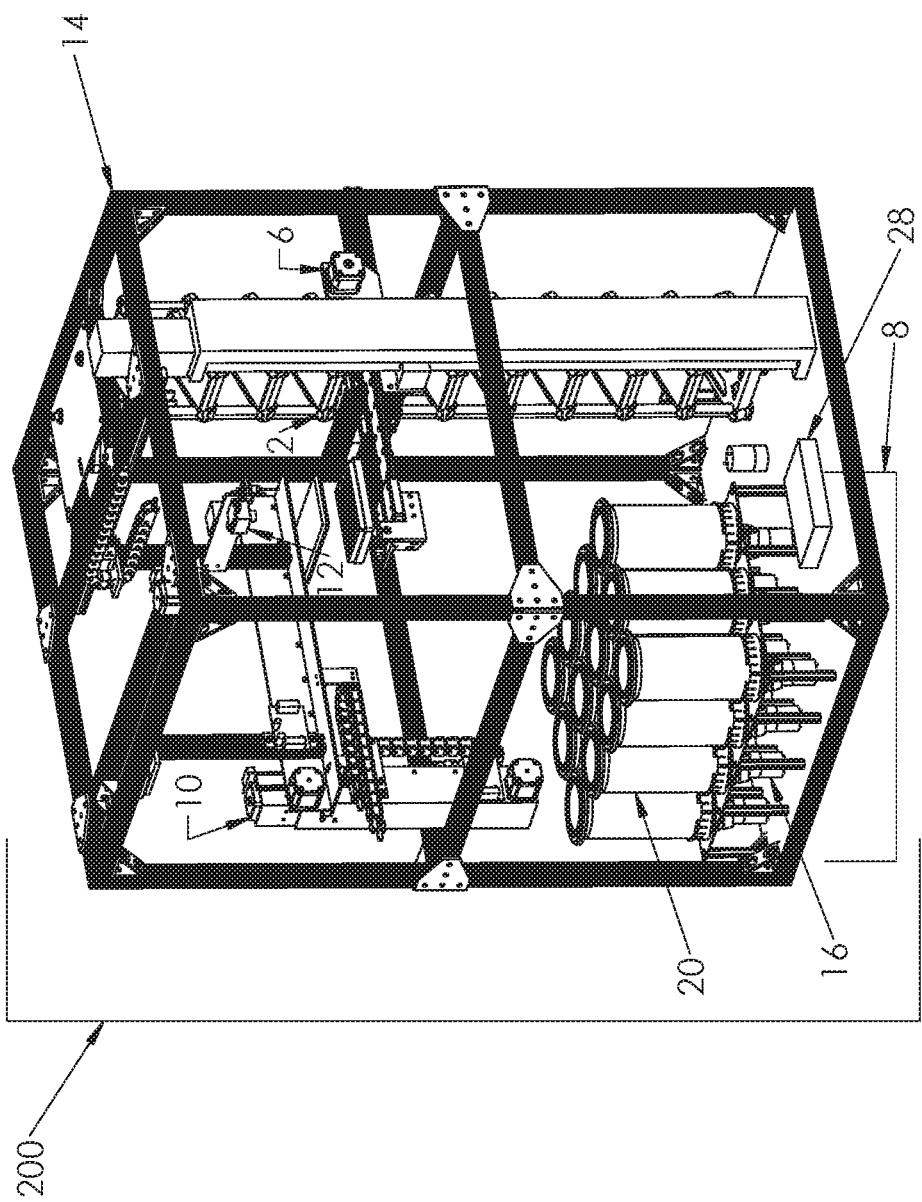
FIG. 1 is a perspective view of an embodiment of a robotic system for culturing and conducting experiments on *C. elegans* in accordance to the principles of the present invention.
Figure 2:
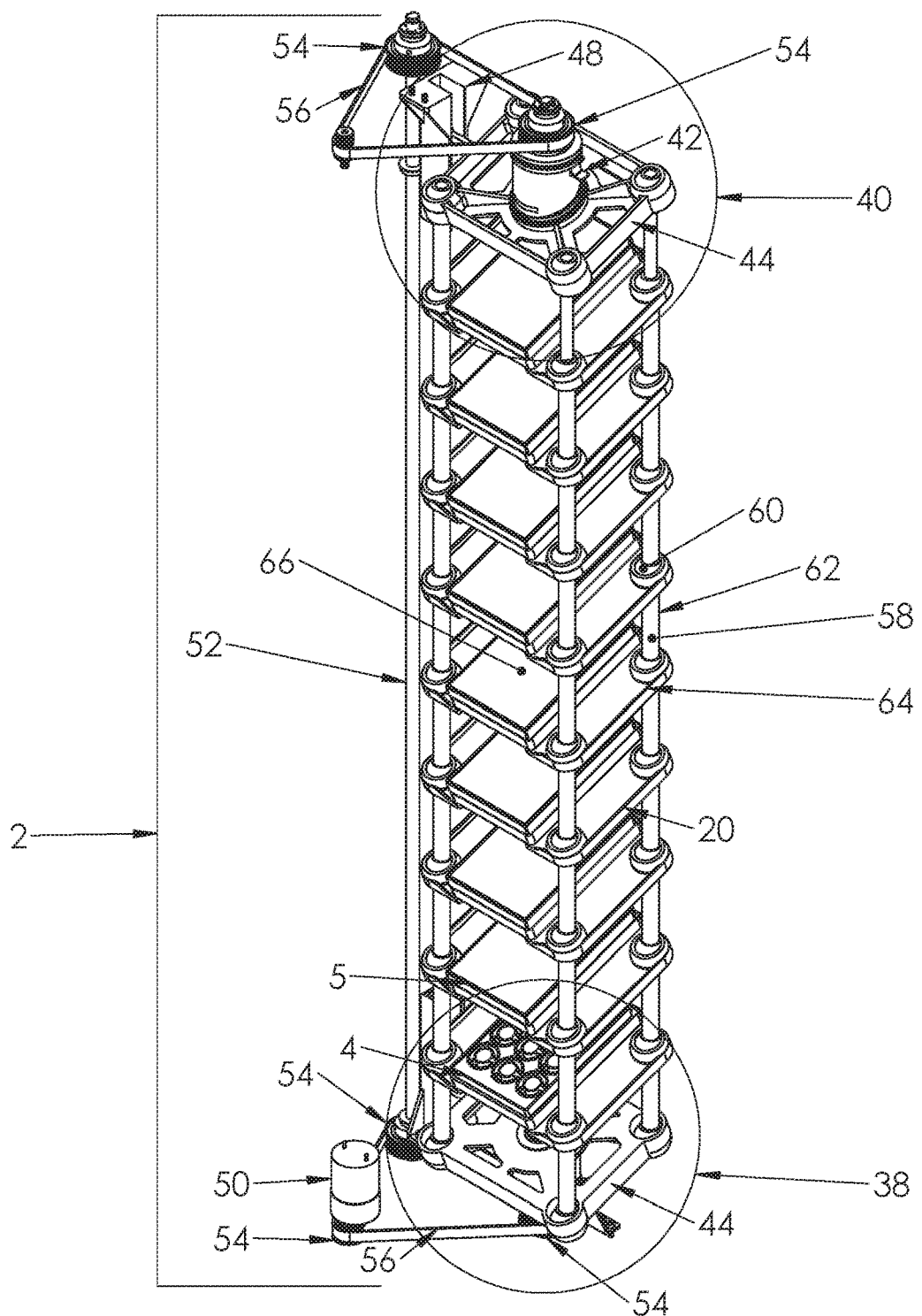
FIG. 2 illustrates a perspective view of the nutating tower of the robotic system shown in FIG. 1.
Figure 3:
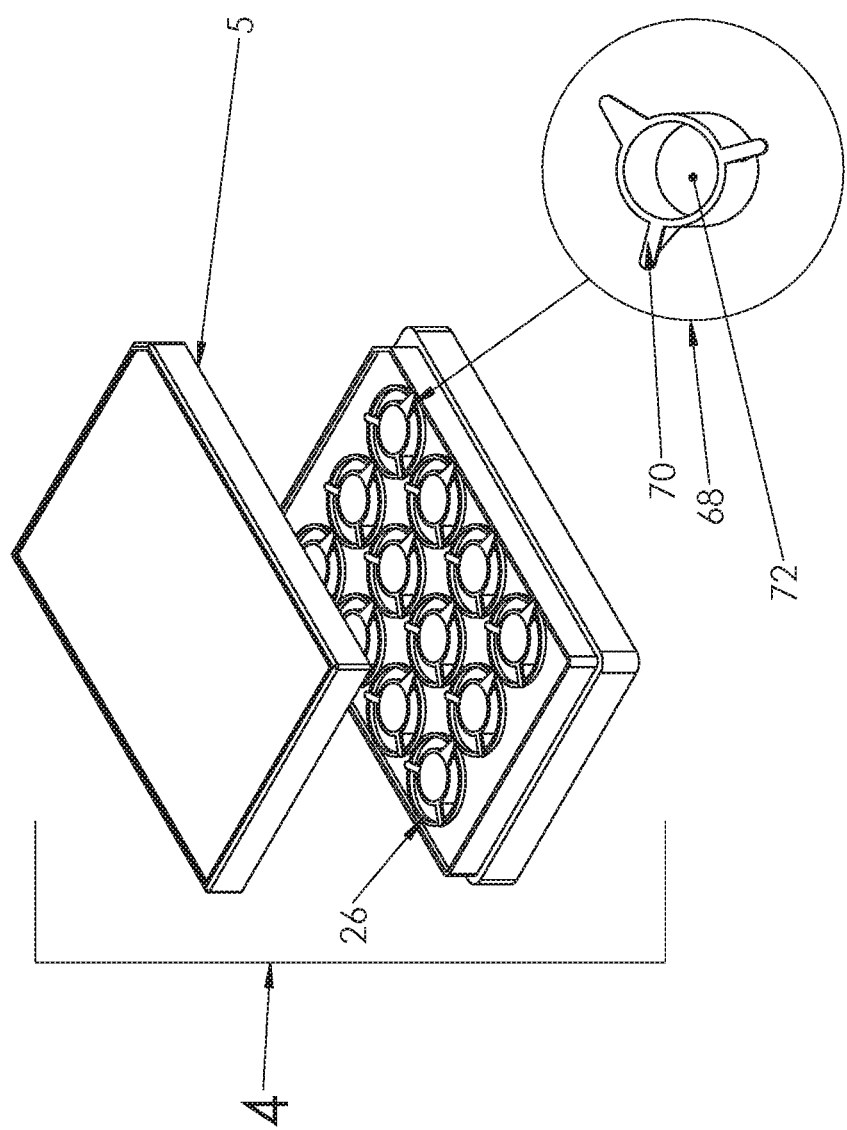
FIG. 3 illustrates a perspective view of a well plate carrying inserts and lid and an individual insert for use with the robotic system shown in FIG. 1.

Referring to FIGS. 1-17, the present invention provides a robotic system 200 that can achieve the above-described steps in an automated fashion with minimal human interaction. The system 200 includes a nutating tower 2 that stores the well plates 4, a well plate positioner 6, a reagent assembly 8, a liquid dispensing assembly 10, a wash and camera assembly 12, a housing assembly 14, a tip tray 17, and a three axes positioner 25. The nutating tower 2 stores the well plates 4. The well-plate positioner 6 manipulates the well plates 4 into various locations. The reagent assembly 8 includes motors 16, each attached to a first magnet 18, that is used to magnetically stir a desired bacterial solution contained within a container 20 when it is magnetically coupled to a second magnet 22 also contained within the container 20. The pipette assembly 10 is constructed to move a liquid dispensing pipette actuator 23 in three axes (x, y, z) in order to dispense desired bacterial solutions from the containers 20 into the wells 26 of the well plate 4 controlled by a robot controller 28. A vacuum needle 30 of the wash and camera assembly 12 is used to remove used bacterial solution contained within each well 26 of the well plate and the buffer needle 32 dispenses a fresh buffer solution to wash the *C. elegans* worms within each well 26 of the well plate 4. After the worms have been cleaned with the buffer solution dispensed from the buffer needle 32, a camera 34 takes a series of pictures of the worms contained in clean buffer solution.

Referring to FIGS. 2 and 9-14, the nutating tower 2 is comprised of a nutating support assembly 36 connected to (i) a base nutating assembly 38 positioned near the bottom of the nutating tower 2, and (ii) a top nutating assembly 40 positioned near the top of the nutating tower 2. Each of the nutating assemblies (38, 40) includes a cylinder 42, a nutating plate 44, a ball 46 located within a ball slot 48 of the nutating support assembly 36. The nutating support assembly 36 includes a motor 50 (e.g., DC motor or the like) that drives a nutating support member 52 and bottom cylinder 42 via one of the belts 56 (part of the base nutating assembly 38). The nutating support member 52, in turn, drives the top cylinder 42 via the other belt 56 (part of top nutating assembly 40).

Figure 14:
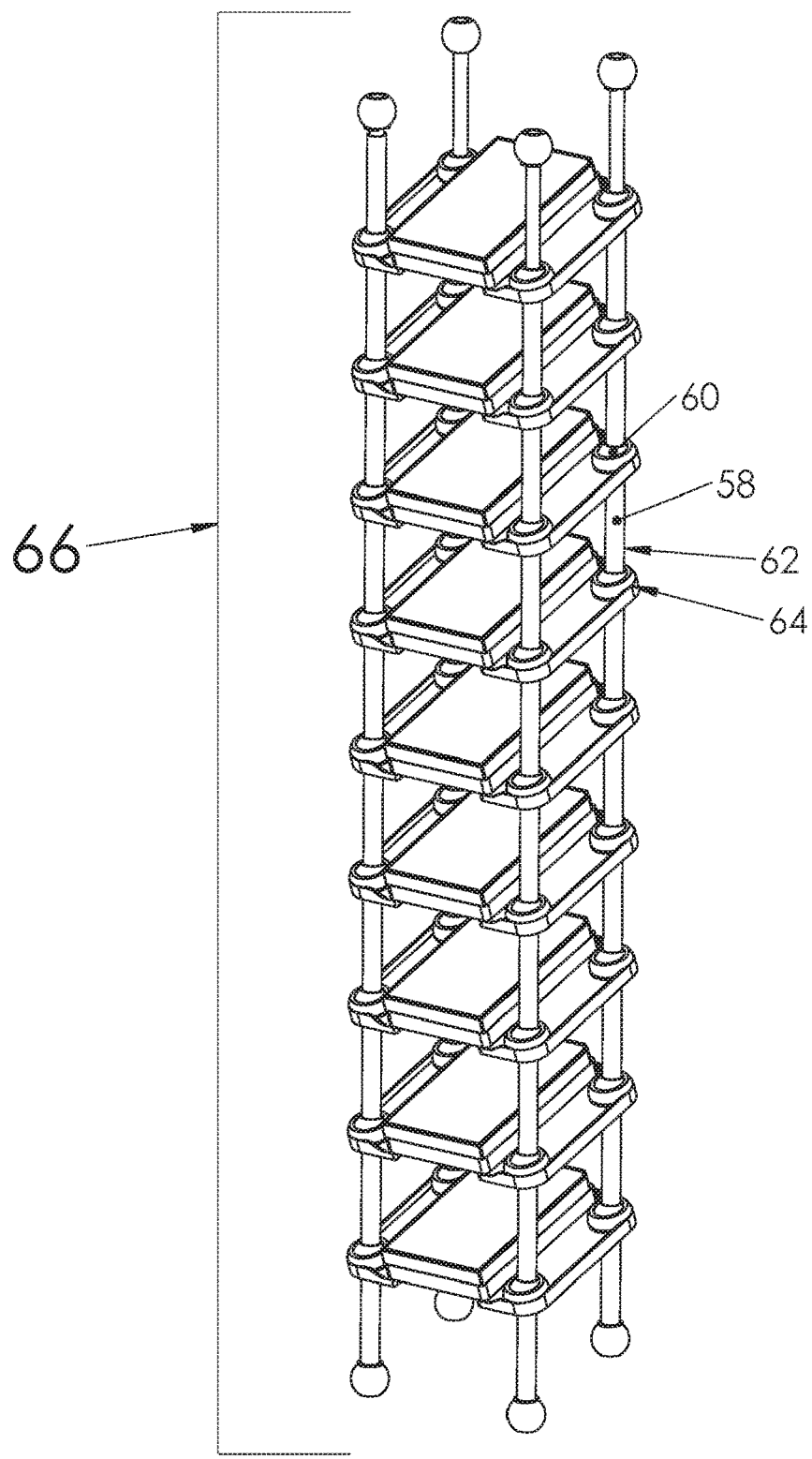
FIG. 14 illustrates a perspective view of the well plate storage unit of the nutating tower shown in FIG. 2.
Figure 15:
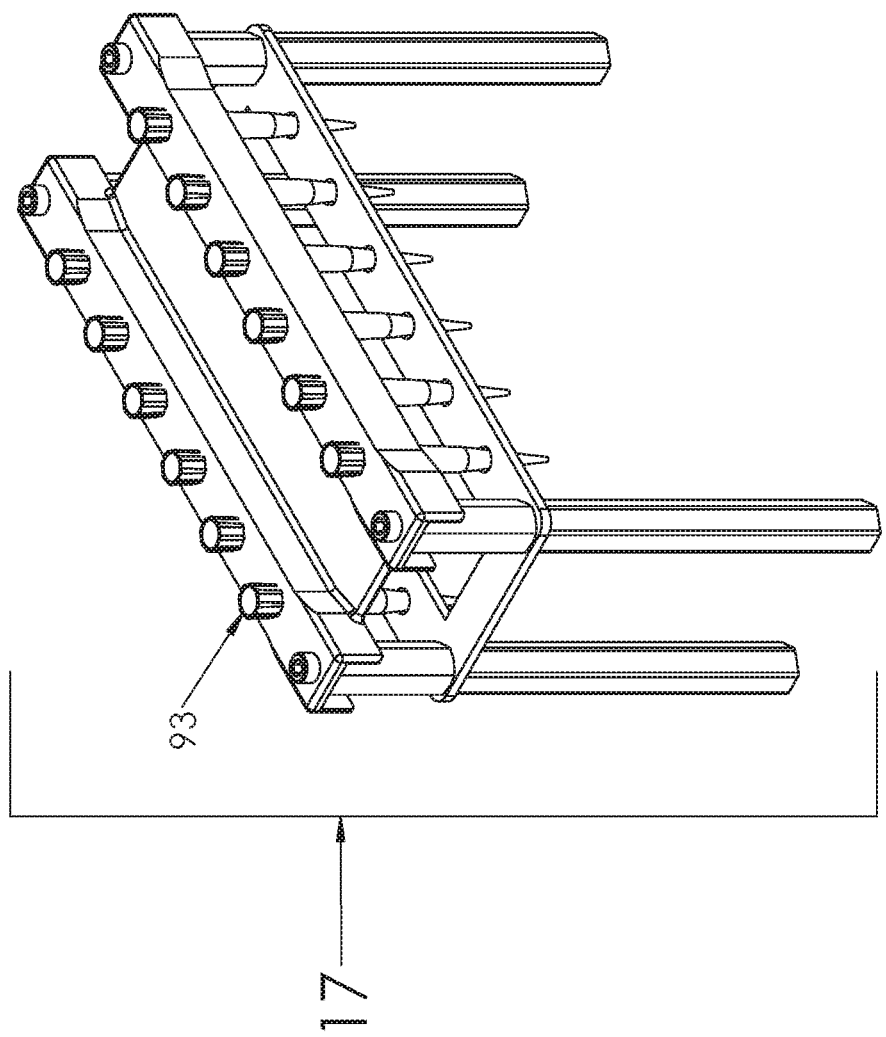
FIG. 15 illustrates a perspective view of the tip tray of the robotic system shown in FIG. 1.
Figure 16:
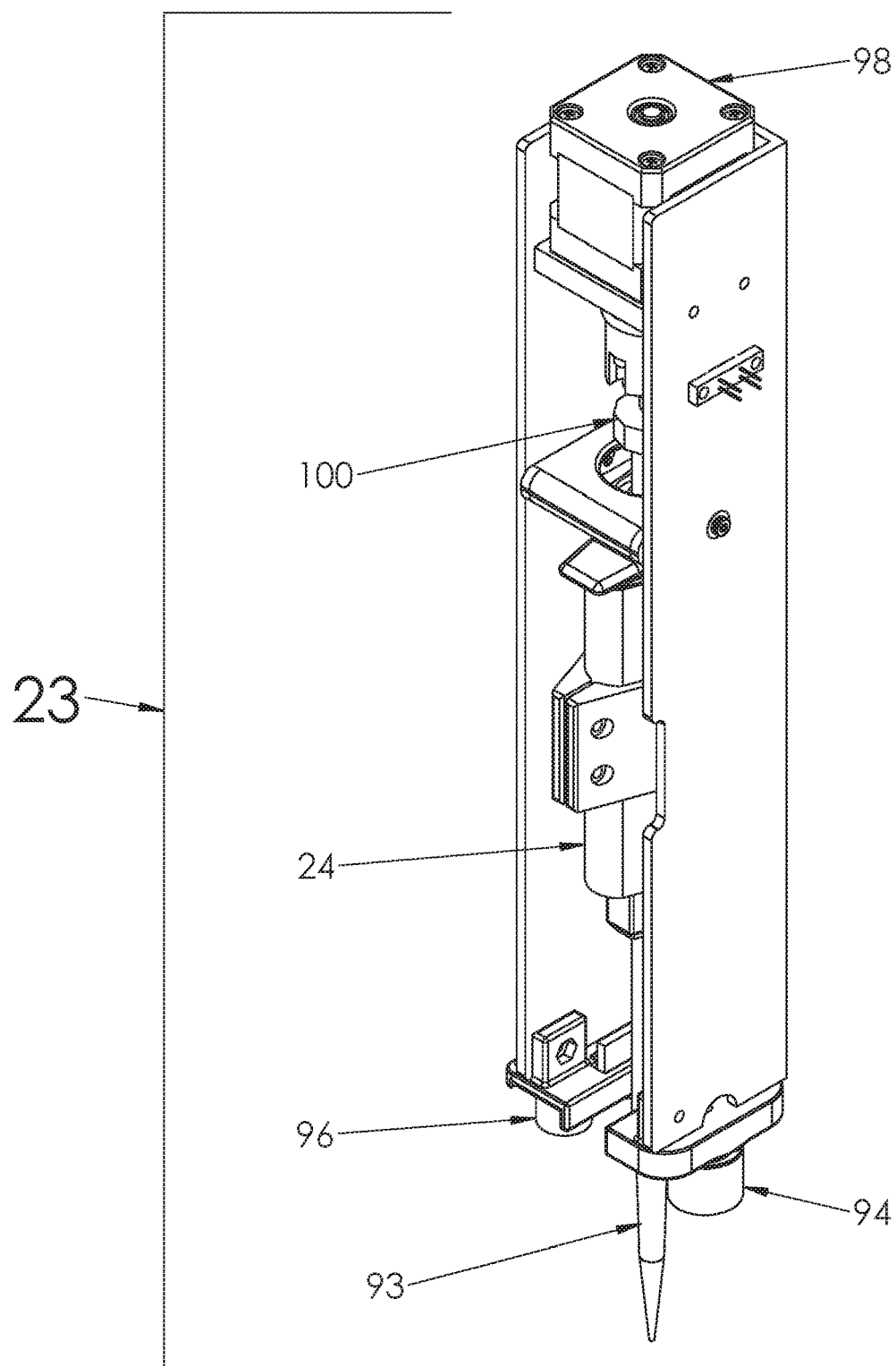
FIG. 16 illustrates a perspective view of the pipette actuator of the liquid dispensing assembly shown in FIG. 4.

When the cylinders 42, which are attached to their respective nutating plates 44, are being rotated by the motor 50, the nutating plates 44 will nutate when they are prevented from rotating by the balls 46. Four rods 58 rod spheres 60, rod spacers 62, and well plate shelves 64 form a well plate storage unit 66 as shown in FIG. 14. Referring to FIGS. 14-15, the rod spacers 62 are threaded onto the rods 58 to support the rod spheres 60, which are threaded on alternately to the rod spacers in a repeating pattern. The well plate shelves 64 includes rod sphere features 63 that sit on the rod spheres 60. The nutating plates 44 cause the four rods 58 to move in a fashion that transfers the nutating motion to all of the well plate shelves 64. Furthermore, the nutating supporting member 52 facilitates the synchronization of the nutating movements of both nutating plates 44 by transferring the angular position of the motor 50 from the nutating plate 44 of the base nutating assembly 38 to the nutating plate 44 of the top nutating assembly 40.

Referring to FIGS. 2-3, and 13-14, in one non-limiting embodiment of the system 200, the well plate storage unit 66 includes ten well plate shelves 64. Each well plate shelf 64 stores one well plate 4. The present invention also contemplates storing more than one well plate 4 on each well plate shelf 64. One skilled in the art can make the necessary adjustments to the system 200 in order to accommodate this alternative embodiment. The well plate 4 is constructed of semi-transparent material (e.g., polycarbonate or the like) and may be any predetermined size. The well plate 4 contains a predetermined number of wells 26. For example and referring to FIG. 3, the well plate 4 can be a standardized well plate containing 12 wells (3×4) such as the CELL-STAR® Cell Culture Multiwell Plates (127.96 cm mm length×85.48 mm width) manufactured by Greiner Bio-One, Germany. The well plate lid 5 includes a portion of magnetic material that assists the removal of the lid 5 from the well plate 4 during process described herein. A culture insert 68 with hangers 70 and a selectively permeable and semi-transparent filter base 72 is placed into each well 26 of the well plate 4. An exemplary embodiment of the culture insert 68 is ThinCert™ manufactured by Greiner Bio-One, Germany. The *C. elegans* worms are cultured within each insert 68. The filter base 72 allows the worms to be easily washed and old bacterial suspension and used washing buffer to be removed. The filter base 72 further allows undesirable *C. elegans* eggs or smaller sized *C. elegans* worms to also be removed during the buffer washes.

Figure 8:
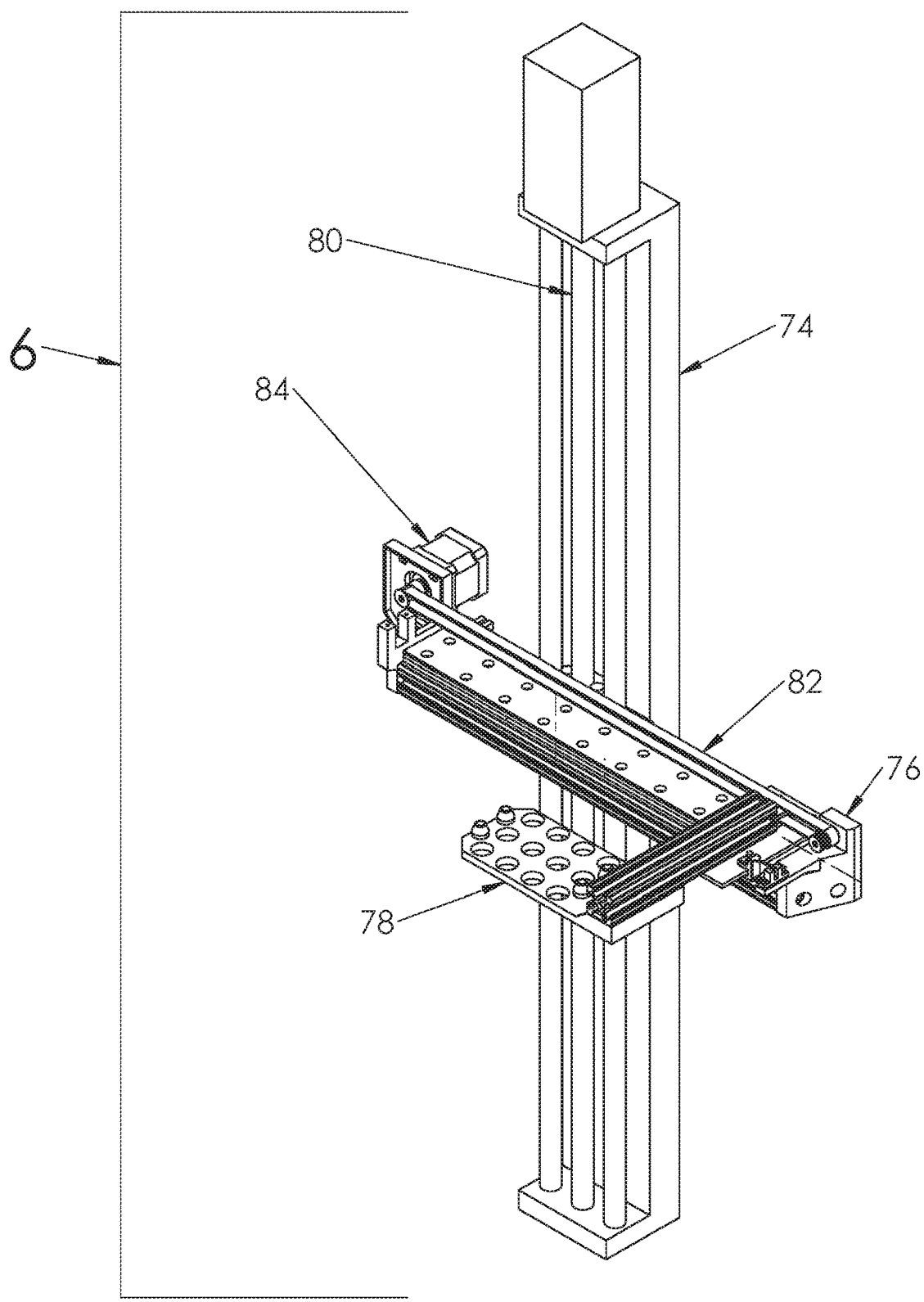
FIG. 8 illustrates a perspective view of the well plate positioner of the robotic system shown in FIG. 1.
Figure 9:
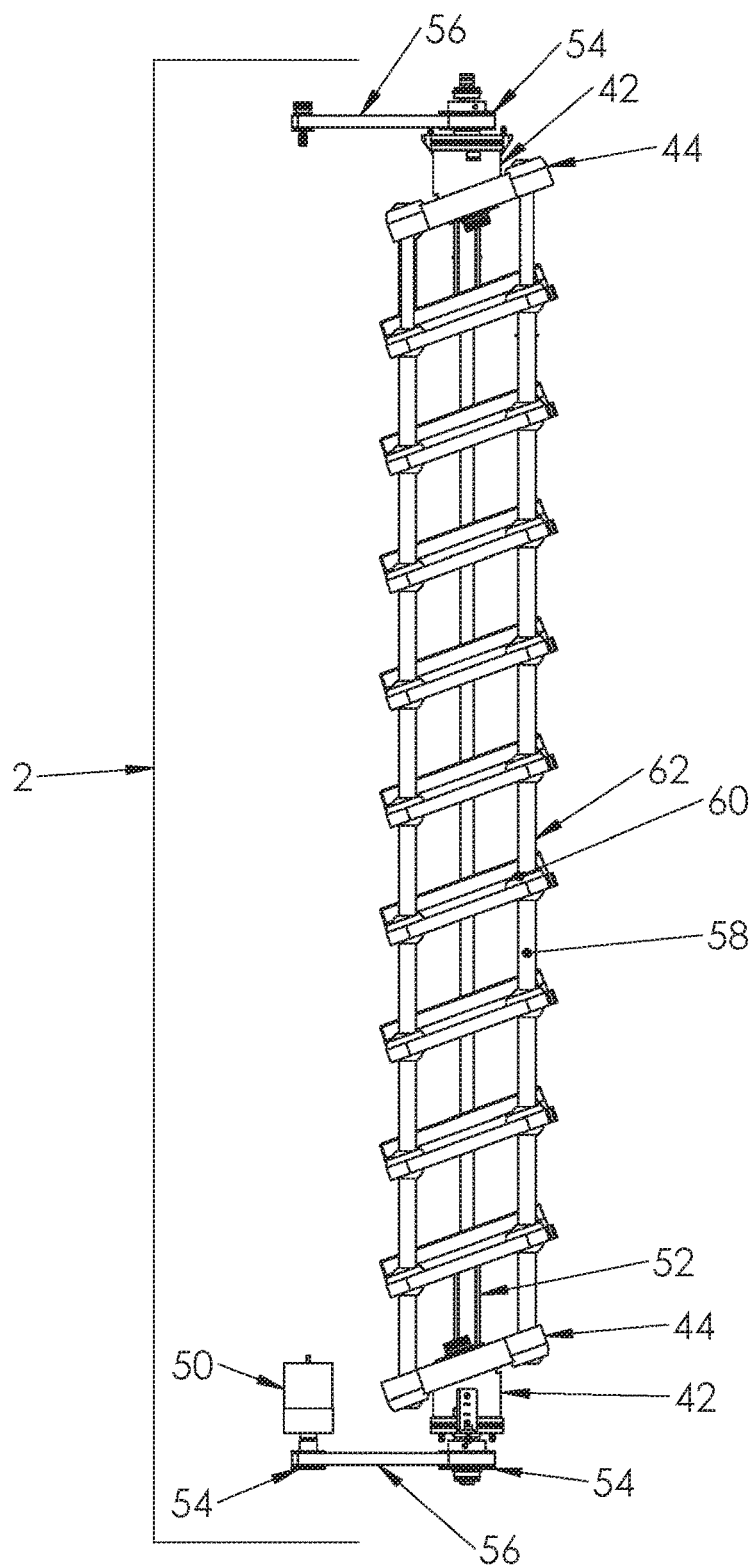
FIG. 9 illustrates a side view of the nutating tower shown in FIG. 2.
Figure 10:
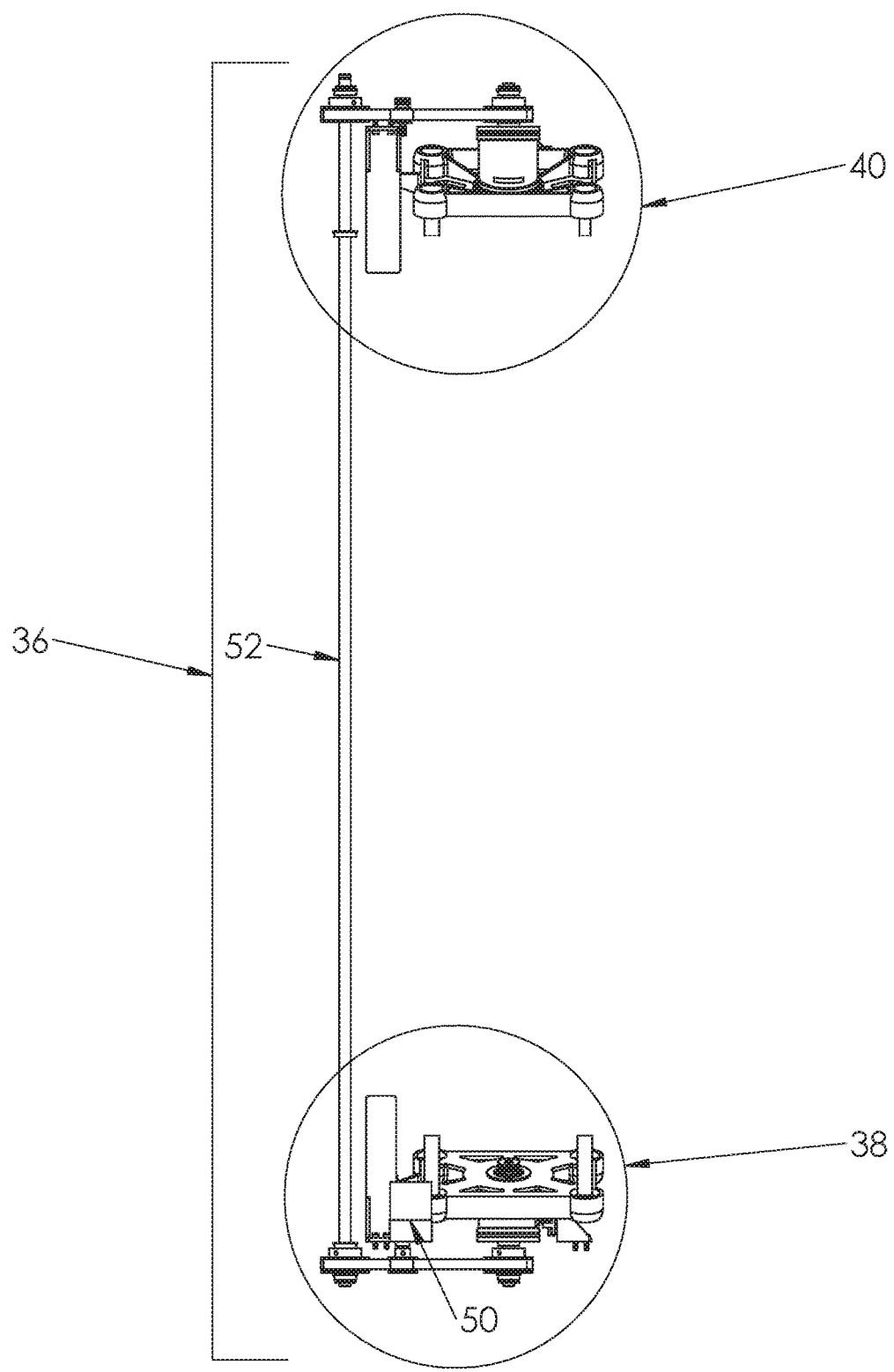
FIG. 10 illustrates a side view of the nutating support assembly of the nutating tower shown in FIG. 9.
Figure 11:
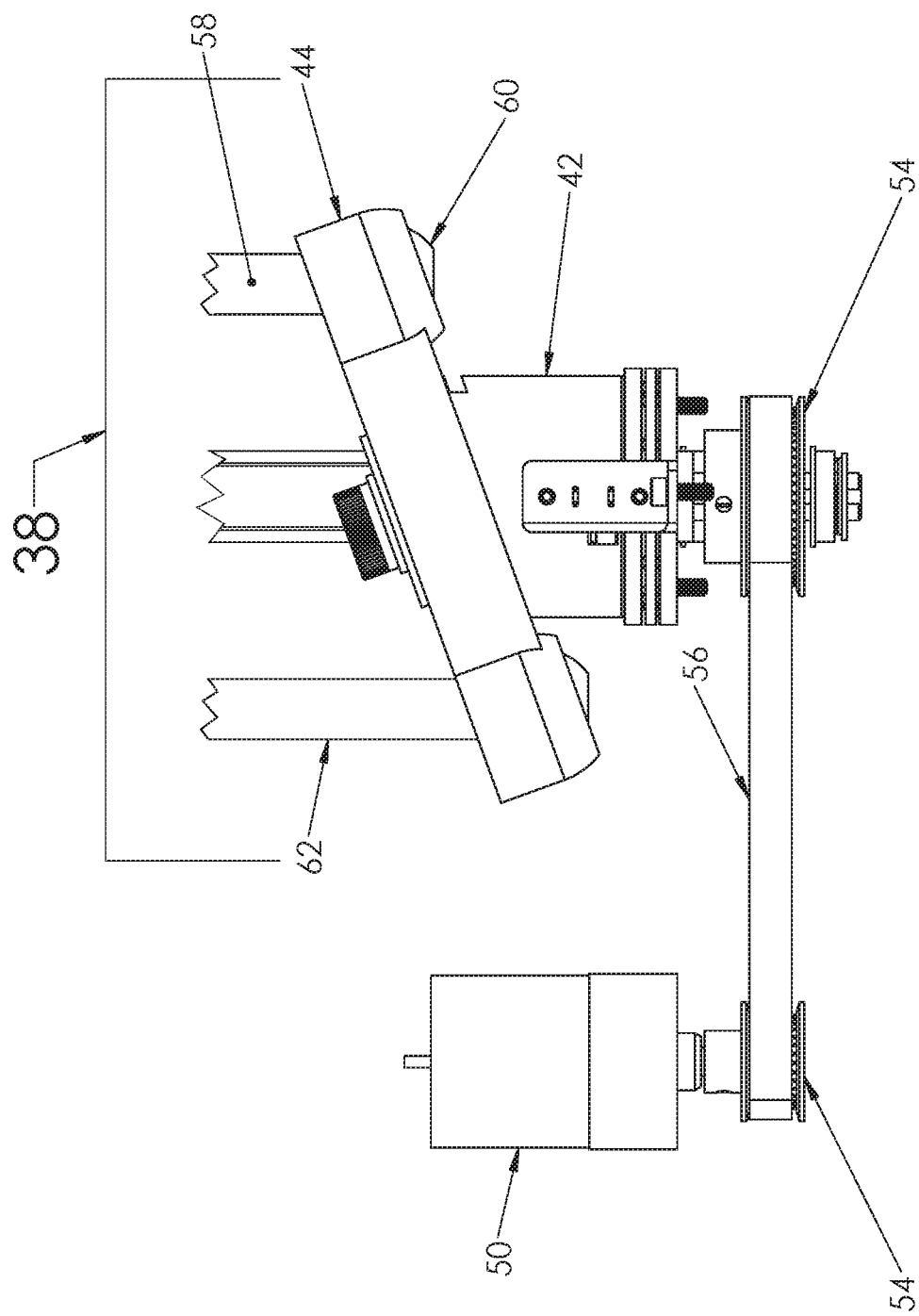
FIG. 11 illustrates a partially sectioned side view of the base portion of the nutating tower shown in FIG. 9.
Figure 12:
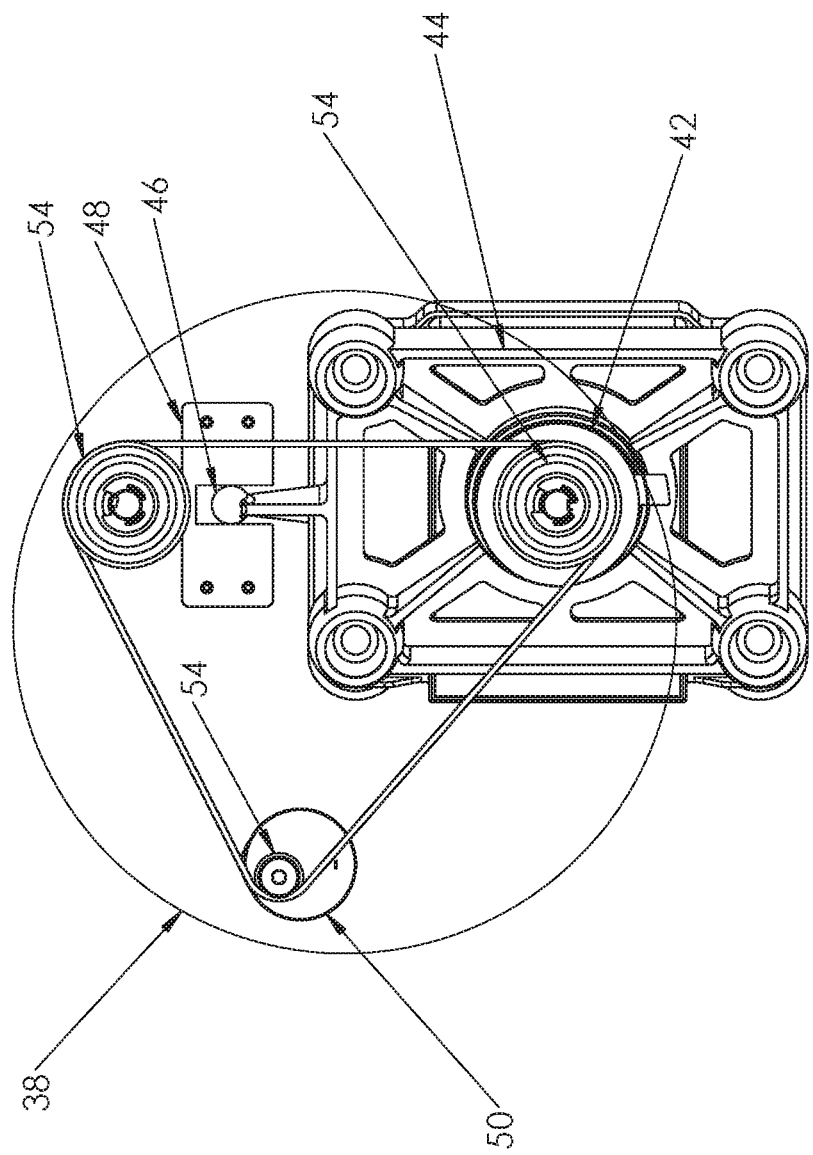
FIG. 12 illustrates a bottom view of the nutating tower shown in FIG. 9.
Figure 13:
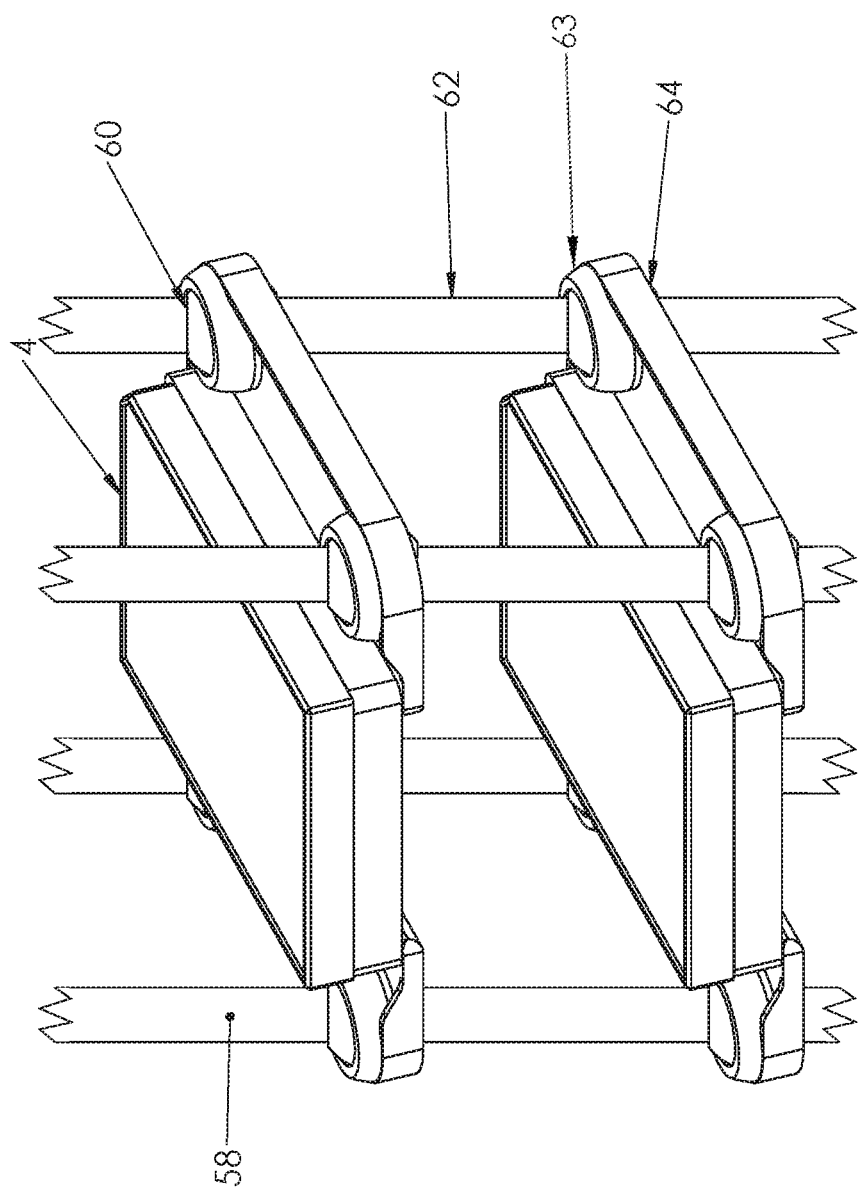
FIG. 13 illustrates a partially sectioned close up perspective view of the nutating tower shown in FIG. 2.

Referring to FIG. 8, the well plate positioner 6 is a robotic arm that moves in two axes. The positioner 6 includes an up and down (e.g., vertical) y-axis positioner 74, a front and back z-axis positioner 76, and a well plate manipulator 78. The y-axis positioner 74 and the z-axis positioner 76 allow the well plate manipulator 78 to move in these two axes in order to retrieve one of the well plates 4 from the nutating tower 2 and to move it (4) to where it (4) will be processed. The y-axis positioner 74 includes a screw drive 80 that moves the well plate manipulator 78 in the y-axis direction. The z-axis positioner 76 includes a belt 82 driven by a stepper motor 84 that moves the well pate manipulator 78 in the z-axis direction. The well plate manipulator 78 holds a well plate 4 in a very accurate and specific way to allow for repeatability in processing.

Figure 5:
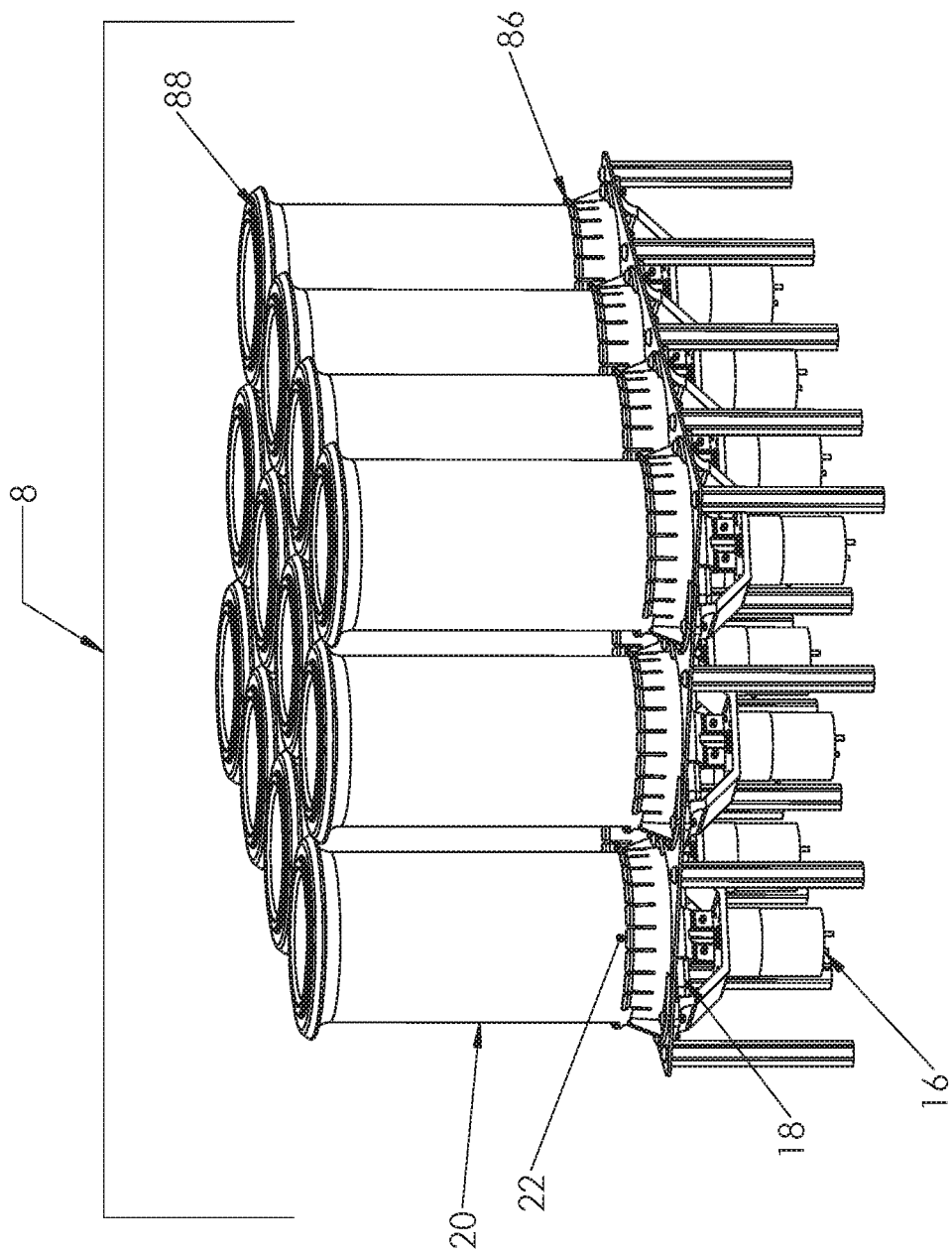
FIG. 5 illustrates a perspective view of the regent assembly of the robotic system shown in FIG. 1.

Referring to FIG. 5, the reagent assembly 8 includes the containers 20, container lids 88, press fit components 86, motors 16, and magnets 18. Each of the containers 20 is held in place with a press fit component 86 that constrains the container 20 to sit directly above its respective motor 16. The motor 16 rotates the first magnet 18 which triggers rotation of the second magnet 22 agitating the bacterial solution contained within the container 20 resulting in the desired bacterial suspension. A lid 88 is provided for each container 20 in order to prevent evaporation of the bacterial solution. The lid 88 contains a portion of magnetic material designed to be magnetically coupled with the pipette electromagnet 94 in order to remove the lid 88 from its container 20.

Figure 4:
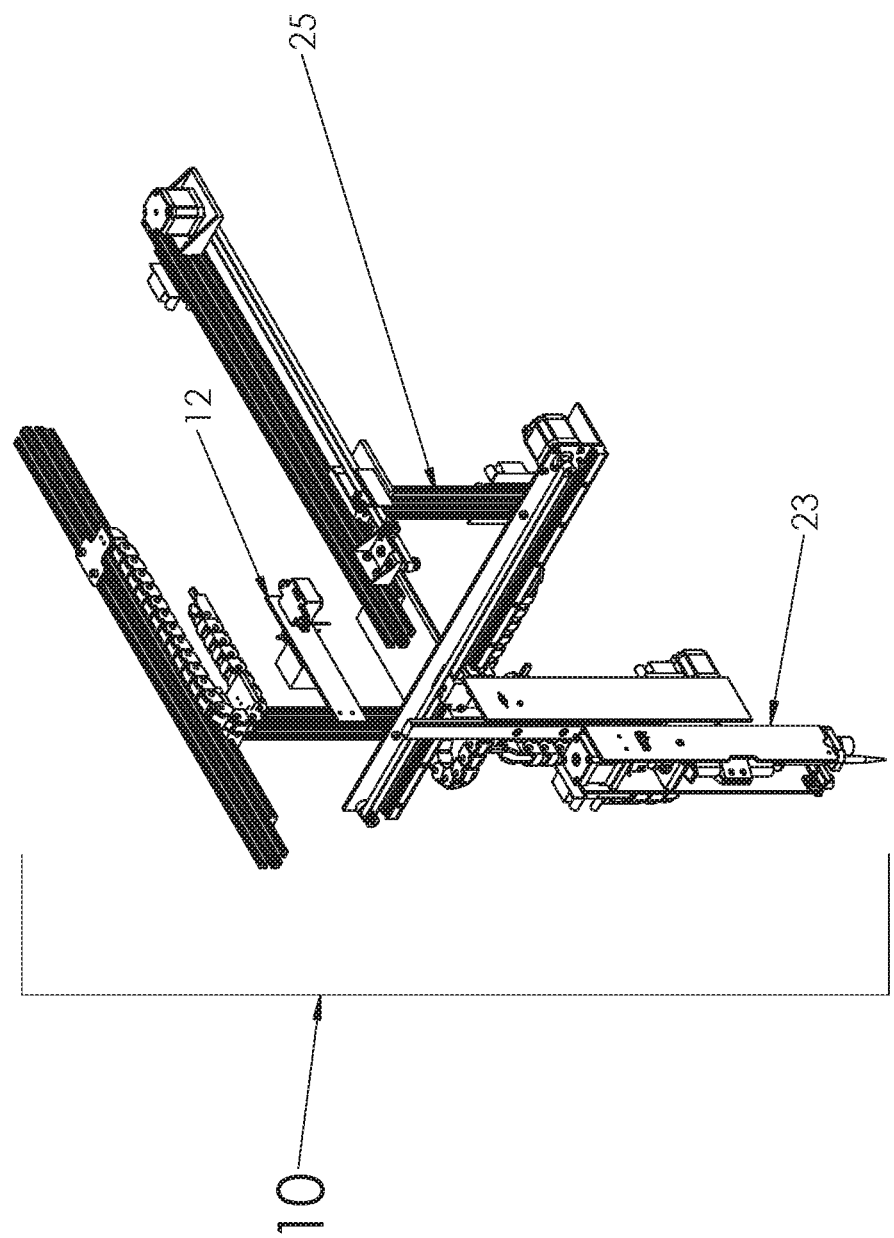
FIG. 4 illustrates a perspective view of the liquid dispensing assembly of the robotic system shown in FIG. 1.

Referring to FIGS. 4-5, the pipette assembly 10 includes the pipette actuator 23 attached to a three axes (x, y, z) positioner 25, which moves the pipette actuator 23 in three axes (x, y, z) in order to dispense desired bacterial solutions from the containers 20 into the wells 26 of the well plate 4 situation on top of the well plate manipulator 78. The three axes positioner 25 includes positioning stepper motors 90 and belts 92. The positioning stepper motors 90 and belts 92 move the pipette actuator 23, attached to the pipette electromagnet 94 to remove the lid 88 by magnetically coupling with the lid 88. The lid 88 is then moved over the other lids 88 and decoupled from the pipette electromagnet 94. Next, the three axes positioner 25 moves the pipette actuator 23 into a specific predetermined location in three dimensions in order to couple with a designated pipette tip 93 stored in the tip tray 17. Once the tip 93 is coupled with the pipette 24, the pipette actuator 23 is moved to the location of a designated container 20 (now without its lid 88). An ultrasonic sensor 96 allows for the detection of the fluid level in the designated container 20 in order to assist in fluid retrieval of the bacterial solution contained within the container 20 by the pipette actuator 23 using its pipette tip 93. A pipette stepper motor 98 controls the plunger 100 of the pipette 24. The plunger 100 is depressed in preparation for the aspiration of the bacterial solution contained in the container 20 into the pipette tip 93. The pipette actuator 23 is dynamically programmable and preferably accurate to at least 10 microliters. After the aspiration, the pipette actuator 23 then moves to the location of a designated well 26 by the three axes positioner 25 and dispenses the bacterial solution contained in the pipette tip 93 into the well 26. This bacterial solution dispensing process is repeated for each designated well 26 contained within the well plate 4 that requires the bacterial solution from the designated container 20. Once it is completed, the three axes positioner 25 moves the pipette actuator 23 to a desired location above the pipette tip's 93 original location within the tip tray 17. The pipette actuator 23 then releases the pipette tip 93 back into its location within the tip tray 17. The three axes positioner 25 then moves to and retrieves the lid 88 by magnetically coupling the pipette electromagnet 94 with the lid, and places the lid 88 back onto the designated container 20.

Figure 6:
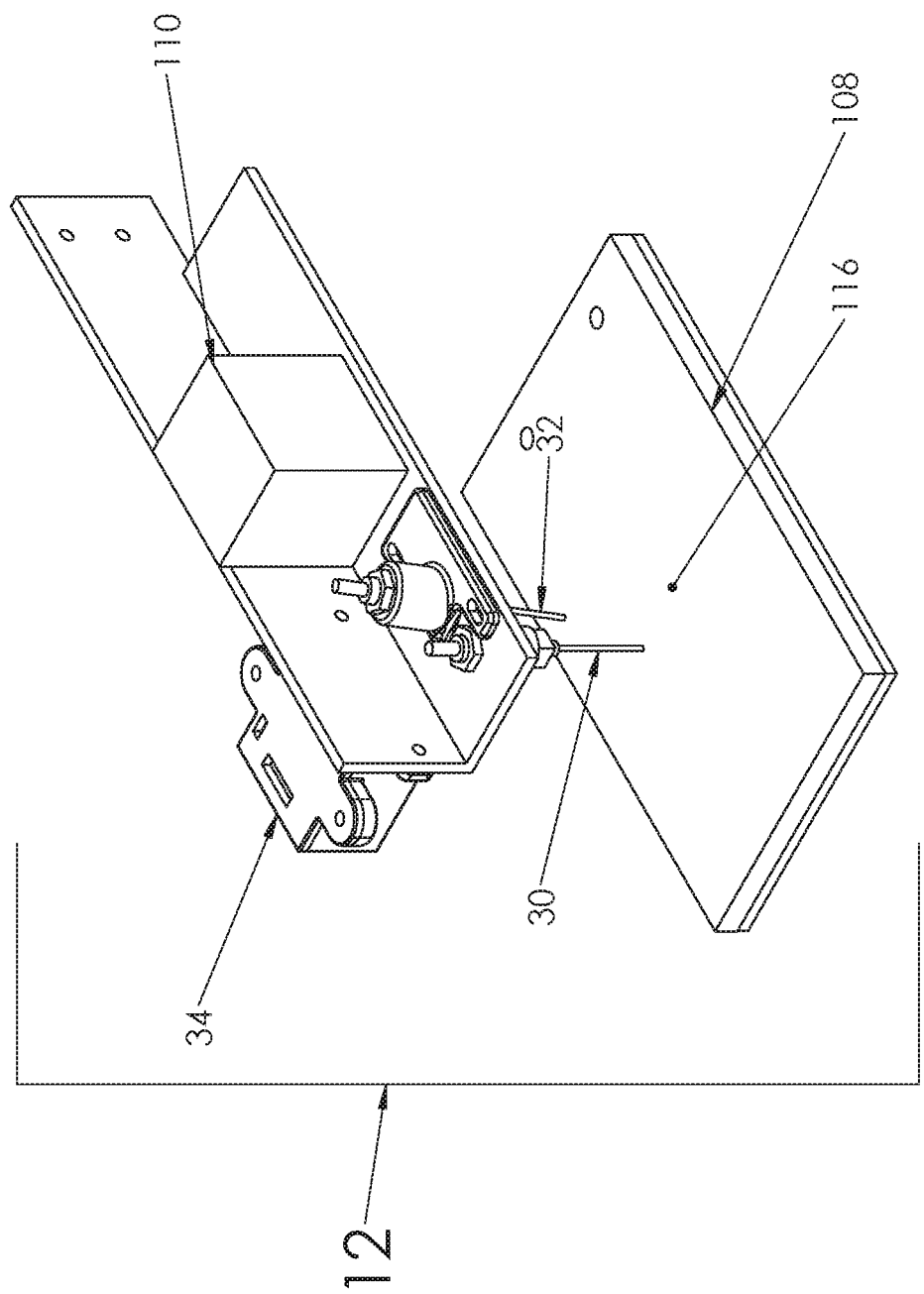
FIG. 6 illustrates a perspective view of the washing and camera assembly of the robotic system shown in FIG. 1.
Figure 7:
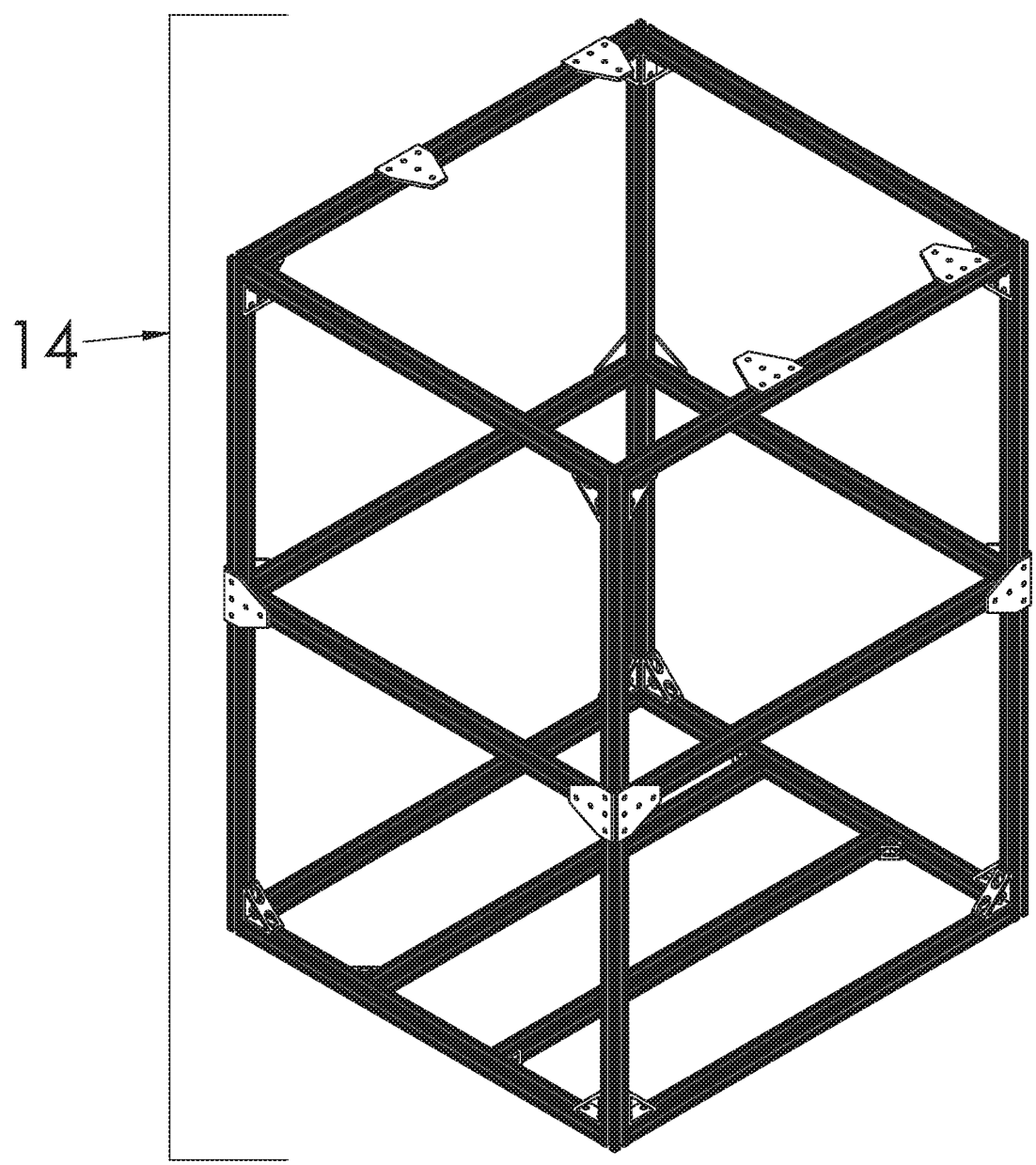
FIG. 7 illustrates a perspective view of the housing assembly of the robotic system shown in FIG. 1.
Figure 17:
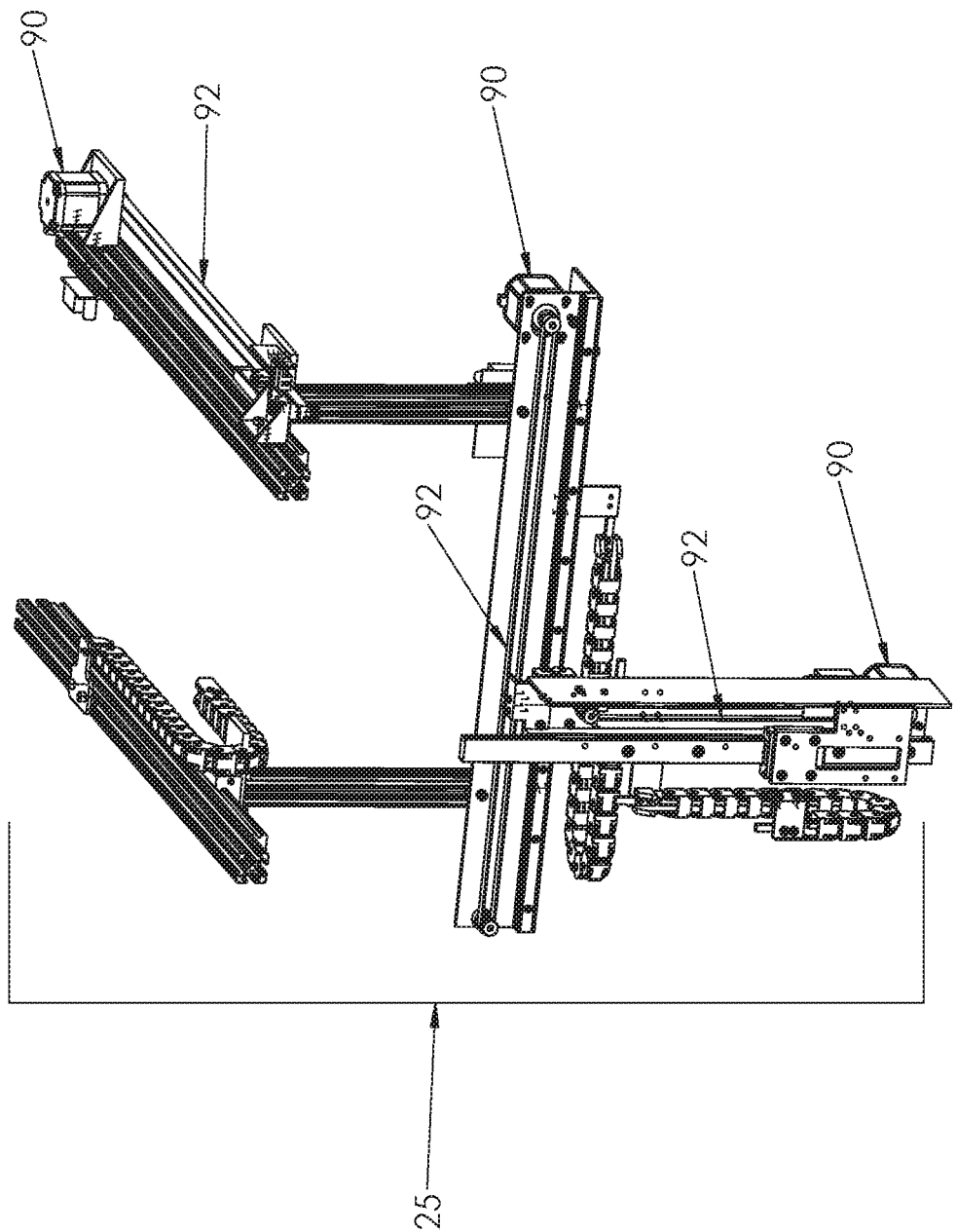
FIG. 17 illustrates a perspective view of the 3D positioner of the liquid dispensing assembly shown in FIG. 4.

Referring to FIGS. 1, 6, 17 the wash and camera assembly 12 is attached to the first tier of the three axes positioner 25, allowing it (12) to move in the x axis. The wash and camera assembly 12 includes the vacuum needle 30, the buffer needle 32, and the camera 34. During operation, the vacuum needle 30 is in fluid communication with a vacuum source in order to provide the desired suction of fluid from a well 26. The buffer needle 32 is in fluid communication with a buffer source to provide the desired dispensation of fresh buffer solution to a well 26. During this washing process, the vacuum needle 30 removes old bacterial solution and used buffer solutions from each well 26 in the well plate 4, while the buffer dispensing needle 32 adds fresh buffer solution to each well for the purposes of cleaning and eventual imaging by the camera 34. A light table 108 helps to illuminate the worms for better photography.

In one embodiment, the system 200 fits into a standard sized incubator in order to keep the temperature constant during the entire process. Alternatively, the system 200 may optionally include an incubator (not shown) to house its other components described herein.

In another embodiment, the system 200 uses a method 300 of the present invention to culture and conduct experiments on the *C. elegans* worms. The method 300 includes placing a predetermined number of the well plates 4 in the well plate shelves 20 of the nutating tower 2. Each well plate 4 having wells 26 containing the worms bathing in bacterial solutions. The method 300 also includes nutating the well plates 4 stored within the nutating tower 2 in order to keep the bacteria in suspension within each well 26. The method 300 further includes stopping the nutating motion of the nutating tower 2 and removing a designated well plate 4 and its lid 5 from its well plate shelf 20 and onto the well plate manipulator 78 using the well plate positioner 6. The well plate manipulator 78 lifts the well plate 4 up from its well plate shelf 20 and then out of the nutating tower 2.

Thereafter, the method 300 includes removing the lid 5 from the well plate 4 using the well plate positioner 6 and the electromagnet 116. The well plate positioner 6 moves the well plate 4 and the lid 5 to a predetermined location wherein the electromagnet 116 magnetically couples with the well plate lid magnet 7. After this coupling, the well plate positioner 6 moves the well plate 4 downward (in y-axis direction) while the lid 5 remains coupled with the electromagnet 116 and removed from the well plate 4.

The method 300 then includes moving the well plate 4 by the well plate positioner 6 to a desired location wherein the vacuum needle 30 is in fluid communication with the bacterial solution inside the designated well 26. This step is achieved by moving the well plate 4 in an upward y-axis direction and the proper z-axis direction toward the vacuum needle 30 using the well plate positioner 6. The vacuum needle 30 is moved to the desired location by the three axes positioner 25. Thereafter, the method 300 includes (i) removing bacterial solution from the designated well 26 by the vacuum needle 30 via the vacuum source; and (ii) providing fresh buffer solution to the well 26 from the buffer source via the buffer needle 32. Finally, the method 300 includes imaging the worms within the well 26 with camera 34. The method steps described in this paragraph are repeated for each well 26 of the well plate 4 containing the worms. The method 300 also includes removing buffer solution from each of the wells 26.

The method 300 further includes adding predetermined fresh bacterial solutions from the containers 20 to each designated well 26 of the well plate 4 located on top of the well plate manipulator 78 using the pipette actuator 23 and the well plate positioner 6. The three axes positioner 25 moves the pipette electromagnet 94 to a desired position so it can magnetically couple with the lid 88. Thereafter, the positioner 25 moves the lid 88 over the other lids 88 and releases the lid 88 by decoupling the lid 88 from the pipette electromagnet 94. Next, the three axes positioner 25 moves the pipette actuator 23 into a specific predetermined location in three dimensions in order to couple with a designated pipette tip 93 stored in the tip tray 17. Once the tip 93 is coupled with the pipette 24, the pipette actuator 23 is moved to the location of a designated container 20 (now without its lid 88). An ultrasonic sensor 96 allows for the detection of the fluid level (e.g., to 1 mm accuracy) in the designated container 20 in order to assist in fluid retrieval of the bacterial solution contained within the container 20 by the pipette actuator 23 using its pipette tip 93. Once the pipette actuator 23 retrieves the desired amount of bacterial solution from the container 20 into its pipette tip 93, it (24) then moves to the location of a designated well 26 and dispenses the bacterial solution into the well by depressing the plunger 100. This bacterial solution dispensing process is repeated for each designated well 26 contained within the well plate 4 that requires the bacterial solution from the designated container 20. Once it is completed, the three axes positioner 25 moves the pipette actuator 23 to a desired location above the pipette tip's 93 original location within the tip tray 17. The pipette actuator 23 then releases the pipette tip 93 back into its location within the tip tray 17. The three axes positioner 25 then moves to the lid storage location 95, retrieves the lid 88 by magnetically coupling it (88) with the pipette electromagnet 94, and places the lid 88 back onto the designated container 20. Thereafter, the entire process described in this paragraph is repeated until each designated well 26 contained the desired amounts of the different bacterial solutions from the containers 20. Please note that each container 20 must have its own corresponding pipette tip 93 stored in the tip tray 17 in order to avoid cross contamination between the bacterial solutions.

Finally, the method 300 includes placing the well plate 4 back into its designated well plate shelf 64 of the nutating tower 10 and nutating the well plate shelves 64. Moreover, all of the steps described herein for the method 300 are controlled by the robot controller 28.

Although the present invention including the system 200 and the method 300 discussed herein are explained using *C. elegans*, it is not limited to culturing and/or experimenting with *C. elegans* alone. The present invention, including the system 200 and the method 300, is applicable to culturing and/or experimenting any other suitable organisms such as other nematodes including but not limited to the entire *Caenorhabditis* genus (e.g., *C. briggsae, C. remanei, C. brenneri, C. angaria*, or the like). For the purpose of this specification, the term "targeted organism(s)" shall be defined as every and all suitable organisms that can be cultured and/or experimented upon by the present invention. Moreover, the present invention is not limited to bacterial solutions discussed above. Instead it contemplates using other suitable solutions for culturing and/or experimenting targeted organisms.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes.

What is claimed is:

1. A robotic system for culturing and conducting experiments on a targeted organism comprising a nutating tower having:
   i. a nutating support assembly comprising a motor, a nutating support member, a top nutating ball slot, and a bottom nutating ball slot;
   ii. a base nutating assembly comprising a base cylinder, a base nutating plate, a base belt, and a base nutating ball;
   iii. a top nutating assembly comprising a top cylinder, a top nutating plate, a top belt and a top nutating ball;
   iv. a well plate storage unit comprising four rods, rod spheres, rod spacers, and well plate shelves wherein (a) the rod spheres and the rob spacers are threaded in an alternate and repeated fashion onto each of the four rods; (b) each of the well plate shelves includes rod sphere features that sit on corresponding rod spheres; and (c) each of the well plate shelves is designed to store at least one well plate;
   v. the motor drives the nutating support member and the bottom cylinder via the base belt;
   vi. the nutating support member when driven by the motor drives the top cylinder via the top belt;
   vii. the base nutating plate is connected to the base cylinder and the base nutating ball is positioned within the base nutating ball slot causing the base nutating plate to nutate in a first direction when the base cylinder is driven by the motor via the base belt;
   viii. the top nutating plate is connected to the top cylinder and the top nutating ball is position within the top nutating ball slot causing the top nutating plate to nutate in the first direction when the top cylinder is driven by the nutating support member via the top belt;
   ix. the nutating supporting member facilitates synchronization of nutation of the top nutating plate and the bottom nutating plate by transferring angular position of the motor from the bottom nutating plate to the top nutating plate; and
   x. the top nutating plate and the bottom nutating plate cause the four rods to move in a fashion that transfer the nutating motion to all of the well plate shelves.

2. The robotic system of claim 1 further comprising: a well plate positioner, a three-axis positioner, a reagent assembly, a liquid dispensing assembly, a washing and camera assembly, a housing assembly, and a tip tray.

3. The robotic system of claim 1 further comprising a well plate positioner comprising a y-axis positioner, a z-axis positioner and a well plate manipulator wherein the y-axis positioner and the z-axis positioner allow the well plate manipulator to move in y-axis direction and z-axis direction in order to retrieve the at least one well plate from the nutating tower to a desired location.

4. The robotic system of claim 3 wherein the y-axis positioner includes a screw drive that moves the well plate manipulator in the y-axis direction; and the z-axis positioner includes a belt driven by a stepper motor that moves the well plate manipulator in the z-axis direction.

5. The robotic system of claim 1 further comprising a reagent assembly having at least one reagent set containing a container, a container lid, a press fits component, a motor, a first magnet, and a second magnet wherein:
   i. the press fits component holds and constrains the container in a desired location directly above the motor;
   ii. the container contains a desired solution for targeted organism;
   iii. the container is covered by the container lid;
   iv. the motor is attached to the first magnet;
   v. the second magnet is located in the container and magnetically coupled to the first magnet;
   vi. when the motor rotates the first magnet, the second magnet also rotates and stirs the desired solution contained within the container.

6. The robotic system of claim 5 further comprising a three axes positioner and a liquid dispensing assembly having a robot controller, and a liquid dispensing pipette actuator wherein (a) the actuator is connected to the three axes positioner in order to dispense the desired solution from the container into wells of the at least one well plate; and (b) the actuator is controlled by the robot controller.

7. The robotic system of claim 6 wherein:
   i. the liquid dispensing assembly further includes a pipette, a pipette electromagnet, and an ultrasonic sensor;
   ii. the three axes positioner moves the actuator and the pipette into a specific predetermined location in three dimensions in order to couple the pipette with a designated pipette tip stored in a tip tray;
   iii. during operation of the robotic system, the pipette electromagnet magnetically couples and magnetically decouples with the container lid; and
   iv. the ultrasonic sensor detects fluid level within the container in order to assist in fluid retrieval of the desired solution contained within the container by the pipette via the pipette tip.

8. The robotic system of claim 1 further comprising a wash and camera assembly having (a) a vacuum needle that removes the desired solution contained within each well of the at least one well plate; (b) a buffer needle dispenses a fresh buffer solution to wash the targeted organism contained within each well of the at least one well plate; and (c) a camera records the targeted organism.

9. The robotic system of claim 1 wherein the targeted organism is *Caenorhabditis elegans*.

10. The robotic system of claim 1 wherein the targeted organism is selected from the group consisting of *Cae-*

*norhabditis elegans, Caenorhabditis briggsae, Caenorhabditis remanei, Caenorhabditis brenneri, Caenorhabditis angaria* and a combination thereof.

11. A robotic system for culturing and conducting experiments on a targeted organism comprising:
   i. a nutating tower having:
      a. a nutating support assembly comprising a motor, a nutating support member, a top nutating ball slot, and a bottom nutating ball slot;
      b. a base nutating assembly comprising a base cylinder, a base nutating plate, a base belt, and a base nutating ball;
      c. a top nutating assembly comprising a top cylinder, a top nutating plate, a top belt and a top nutating ball;
      d. a well plate storage unit comprising four rods, rod spheres, rod spacers, and well plate shelves wherein (1) the rod spheres and the rob spacers are threaded in an alternate and repeated fashion onto each of the four rods; (2) each of the well plate shelves includes rod sphere features that sit on corresponding rod spheres; and (3) each of the well plate shelves is designed to store at least one well plate;
      e. the motor drives the nutating support member and the bottom cylinder via the base belt;
      f. the nutating support member when driven by the motor drives the top cylinder via the top belt;
      g. the base nutating plate is connected to the base cylinder and the base nutating ball is positioned within the base nutating ball slot causing the base nutating plate to nutate in a first direction when the base cylinder is driven by the motor via the base belt;
      h. the top nutating plate is connected to the top cylinder and the top nutating ball is positioned within the top nutating ball slot causing the top nutating plate to nutate in the first direction when the top cylinder is driven by the nutating support member via the top belt;
      i. the nutating supporting member facilitates synchronization of nutation of the top nutating plate and the bottom nutating plate by transferring angular position of the motor from the bottom nutating plate to the top nutating plate; and
      j. the top nutating plate and the bottom nutating plate cause the four rods to move in a fashion that transfers the nutating motion to all of the well plate shelves;
   ii. a well plate positioner comprising a y-axis positioner, a z-axis positioner and a well plate manipulator wherein the y-axis positioner and the z-axis positioner allow the well plate manipulator to move in y-axis direction and z-axis direction in order to retrieve the at least one well plate from the nutating tower to a desired location;
   iii. a reagent assembly having at least one reagent set containing a container, a container lid, a press fits component, a motor, a first magnet, and a second magnet wherein:
      a. the press fits components holds and constrains the container in a desired location directly above the motor;
      b. the container contains a desired solution for targeted organism;
      c. the container is covered by the container lid;
      d. the motor is attached to the first magnet;
      e. the second magnet is located in the container and magnetically coupled to the first magnet; and
      f. when the motor rotates the first magnet, the second magnet also rotates and stirs the desired solution contained within the container;
   iv. a three axes positioner;
   v. a liquid dispensing assembly having a robot controller, and a liquid dispensing pipette actuator wherein:
      a. the actuator is connected to the three axes positioner in order to dispense the desired solution from the container into wells of the at least one well plate; and
      b. the actuator is controlled by the robot controller;
   vi. a wash and camera assembly having:
      a. a vacuum needle that removes the desired solution contained within each well of the at least one well plate;
      b. a buffer needle dispenses a fresh buffer solution to wash the targeted organism contained within each well of the at least one well plate; and
      c. a camera records the targeted organism.

12. The robotic system of claim 11 wherein the y-axis positioner includes a screw drive that moves the well plate manipulator in the y-axis direction; and the z-axis positioner includes a belt driven by a stepper motor that moves the well pate manipulator in the z-axis direction.

13. The robotic system of claim 11 wherein:
   i. the liquid dispensing assembly further includes a pipette, a pipette electromagnet, and an ultrasonic sensor;
   ii. the three axes positioner moves the pipette actuator and the pipette into a specific predetermined location in three dimensions in order to couple the pipette with a designated pipette tip stored in a tip tray;
   iii. during operation of the robotic system, the pipette electromagnet magnetically couples and magnetically decouples with the container lid; and
   iv. the ultrasonic sensor detects fluid level within the container in order to assist in fluid retrieval of the desired solution contained within the container by the pipette via the pipette tip.

14. The robotic system of claim 11 wherein the targeted organism is *Caenorhabditis elegans*.

15. The robotic system of claim 11 wherein the targeted organism is selected from the group consisting of *Caenorhabditis elegans, Caenorhabditis briggsae, Caenorhabditis remanei, Caenorhabditis brenneri, Caenorhabditis angaria* and a combination thereof.

16. A method of using a robotic system to culture and conduct experiments on a targeted organism comprising:
   i. providing a robotic system having a nutating tower, a well plate positioner, a reagent assembly, a liquid dispensing assembly, a wash and camera assembly, a housing assembly, a tip tray, and a three axes positioner;
   ii. placing a predetermined number of well plates having wells containing the targeted organism bathing in predetermined desired solutions, into the nutating tower, wherein each of the well plates is covered by a well plate lid;
   iii. nutating the well plates stored within the nutating tower;
   iv. stopping the nutating motion of the nutating tower and removing a designated well plate from the well plates stored in the nutating tower using the well plate positioner;
   v. removing the well plate lid from the designated well plate using the well plate positioner and an electromagnet;

vi. removing the desired solution from a designated well of the removed well plate by a vacuum needle of the washing and camera assembly;
vii. washing the targeted organism in the well by providing fresh buffer solution to the designated well via a buffer needle of the washing and camera assembly and thereafter removing the buffer solution and repeating this step for at least two times;
viii. providing fresh buffer solution to the designated well;
ix. imaging the targeted organism within the designated well with a camera of the washing and camera assembly;
x. removing the buffer solution from the designated well;
xi. applying step v to step ix to each of the wells of the well plate containing the targeted organism;
xii. adding predetermined fresh desired solutions from the reagent assembly to each of the designated wells using the liquid dispensing assembly and the well plate positioner;
xiii. placing the well plate back into the nutating tower;
xiv. nutating the well plates stored within the nutating tower nutating the well plate shelves; and
xv. applying step iii to step xiv to all of the designated well plates stored in the nutating tower.

17. The method of claim 16 wherein the nutating tower is comprised of:
   i. a nutating support assembly comprising a motor, a support member, a top nutating ball slot, and a bottom nutating ball slot;
   ii. a base nutating assembly comprising a base cylinder, a base nutating plate, a base belt, and a base nutating ball;
   iii. a top nutating assembly comprising a top cylinder, a top nutating plate, a top belt and a top nutating ball;
   iv. a well plate storage unit comprising four rods, rod spheres, rod spacers, and well plate shelves wherein (1) the rod spheres and the rob spacers are threaded in an alternate and repeated fashion onto each of the four rods; (2) each of the well plate shelves includes sphere features that sit on corresponding rod spheres; and (3) each of the well plate shelves is designed to store at least one well plate;
   v. the motor drives the nutating support member and the bottom cylinder via the base belt;
   vi. the nutating support member when driven by the motor drives the top cylinder via the top belt;
   vii. the base nutating plate is connected to the base cylinder and the base nutating ball is positioned within the base nutating ball slot causing the base nutating plate to nutate in a first direction when the base cylinder is driven by the motor via the base belt;
   viii. the top nutating plate is connected to the top cylinder and the top nutating ball is position within the top nutating ball slot causing the top nutating plate to nutate in the first direction when the top cylinder is driven by the nutating support member via the top belt;
   ix. the nutating supporting member facilitates synchronization of nutation of the top nutating plate and the bottom nutating plate by transferring angular position of the motor from the bottom nutating plate to the top nutating plate; and
   x. the top nutating plate and the bottom nutating plate cause the four rods to move in a fashion that transfers the nutating motion to all of the well plate shelves.

18. The method of claim 16 wherein
   i. the liquid dispensing assembly further includes a pipette, a pipette electromagnet, and an ultrasonic sensor;
   ii. the three axes positioner moves the pipette actuator and the pipette into a specific predetermined location in three dimensions in order to couple the pipette with a designated pipette tip stored in a tip tray;
   iii. during operation of the robotic system, the pipette electromagnet magnetically couples and magnetically decouples with the container lid; and
   iv. the ultrasonic sensor detects fluid level within the container in order to assist in fluid retrieval of the desired solution contained within the container by the pipette via the pipette tip.

19. The method of claim 16 wherein the targeted organism is *Caenorhabditis elegans*.

20. The method of claim 16 wherein the targeted organism is selected from the group consisting of *Caenorhabditis elegans, Caenorhabditis briggsae, Caenorhabditis remanei, Caenorhabditis brenneri, Caenorhabditis angaria* and a combination thereof.

* * * * *